United States Patent [19]
Hampar et al.

[11] Patent Number: 4,465,769
[45] Date of Patent: Aug. 14, 1984

[54] NON-TRANSFORMED THYMIDINE KINASELESS CELL LINE AND ITS USE FOR TESTING TUMORIGENIC POTENTIAL OF GENES

[75] Inventors: Berge Hampar, Middletown; Stephen D. Showalter, Gaithersburg, both of Md.

[73] Assignee: The United States of America as represented by the Department of Health and Human Services, Washington, D.C.

[21] Appl. No.: 329,870

[22] Filed: Dec. 11, 1981

[51] Int. Cl.$^3$ .......................... C12Q 1/68; C12Q 1/29; C12N 15/00; C12N 5/00

[52] U.S. Cl. .......................................... 435/6; 435/5; 435/29; 435/34; 435/240; 435/235; 435/948; 435/172.1; 935/57

[58] Field of Search .................. 435/29, 34, 235, 236, 435/172, 240, 948, 5, 4, 6, 1 S

[56] References Cited

U.S. PATENT DOCUMENTS

| | | | |
|---|---|---|---|
| 4,066,510 | 1/1978 | Thilly | 435/29 |
| 4,302,535 | 11/1981 | Skopek et al. | 435/29 |
| 4,399,216 | 8/1983 | Axel et al. | 435/948 |

OTHER PUBLICATIONS

Hampar et al., "Herpes Simplex Virus (Type 1) Thymidine Kinase Gene does not Transform Cells Morphologically," Proceedings of the National Academy of Sciences 78(4) (4–1981), pp. 2616–2619.
Kit et al., "Deletion of Thymidine Kinase Activity from L Cells Resistant to Bromodeoxyuridine", Experimental Cell Research 31 (1963), pp. 297–312.
Mantei et al., "Rabbit B–Globin mRNA Production in Mouse L Cells Transformed with Cloned Rabbit B-Globin Chromosomal DNA," Nature, 281 (Sep. 6, 1979), pp. 40–46.
Wigler et al., "Transformation of Mammalian Cells with Genes From Procaryote and Eucaryotes," Cell, vol. 16 (1979), pp. 777–785.
Topp, "Normal Rat Cell Lines Deficient in Nuclear Thymidine Kinase," Virology vol. 133 (1981), pp. 408–411.
Lai et al., "Ovalbumin is Synthesized in Mouse Cells Transformed with the Natural Check Ovalbumin Gene", Proceedings of the National Academy of Sciences, vol. 77(1), (1980), pp. 244–248.
Chen et al., "Characterization of Pyrimidine Deoxyribonucleoside Kinase (Thymidine Kinase) and Thymicylate Kinase as a Multifunctional . . . ", Journal of Virology 30(3), (1979), pp. 942–945.
Davidson et al., "Herpes Simplex Virus as a Source of Thymidine Kinase for Thymidine Kinase Deficient Mouse Cells", Proc. Nat. Acad. Sci. USA 70(7), (1973), pp. 1912–1916, Chem. Abst. 79:64128m.
Kit et al., "Biochemical Transformation of Thymidine Kinase (TK) Deficient Mouse Cells by Herpes Simplex Virus Type 1 DNA Fragments", Nucleic Acids Research, 8(22), (1980), pp. 5233–5253, Chem. Abst. 94:59960g.
Warrick et al., "DNA Mediated Cotransfer of Unlinked Mammalian Cell Markers into Mouse L Cells," Journal of Cell Biology 86(1), (1980), pp. 341–346, Chem. Abst. 94:28077v.
Mazger–Freed, "Thymidine Kinase Deficiency in Cultured Haploid Cells: Gene Mutation or Regulation?", Prog. Differ. Res. Proc., Int. Confer. (1975), pp. 189–196, Chem. Abst. 85:120260m.
Littlefield, "Selection of Hybrids from Matings of Fibroblasts in Vitro", Science 145 (1964), pp. 709–710.
Cheng et al., "Mouse Ascites Sarcoma 180 Deoxythymidine Kinase, General Properties and Inhibition Studies", Biochemistry 13(6), (1974), pp. 1179–1185.
Hampar et al., "Comparison of Properties of Mouse Cells Transformed Spontaneously by Ultraviolet Light--Irradiated Herpes . . . ", Cancer Research 40 (1980), pp. 2213–2222.
Bacchetti et al., "Transfer of the Gene for Thymidine Kinase to Thymidine Kinase Deficient Human Cells by Puridied Herpes Simplex", Proceedings of the National Academy of Sciences 74(4), pp. 1590–1594.

Primary Examiner—Thomas G. Wiseman
Assistant Examiner—John Edward Tarcza
Attorney, Agent, or Firm—John S. Roberts, Jr.

[57] ABSTRACT

A non-transformed cell line is produced by treating BALB/c derived 10E2 cells with 5-bromodeoxyuridine and 5-iodo-2'-deoxyuridine to produce thymidine kinaseless cells which upon multiple cloning show a flat epitheloid appearance indicative of their non-transforming potential. These cells are used to determine the tumorigenic transforming potential of any gene by introducing the gene into the cells of the non-transformed cell line along with the Herpes simplex virus thymidine kinase gene which serves as a vehicle for cotransfection. The transformation of the cells is indicative of tumorigenic potential.

9 Claims, No Drawings

NON-TRANSFORMED THYMIDINE KINASELESS CELL LINE AND ITS USE FOR TESTING TUMORIGENIC POTENTIAL OF GENES

STATEMENT OF PRIOR ART

Kit et al, *Experimental Cell Research*, 31:297–312 (1963) teaches preparation of cells deleted of thymidine kinase.

Bacchetti and Graham, *Proc. Natl. Acad. Sci.*, Vol. 74, No. 4, 1590–1594 (1977) discusses the transfer of the gene for thymidine kinase to thymidine kinase-deficient human cells by herpes simplex viral DNA.

Mantei et al, *Nature*, 281:40–46, discusses mouse thymidine kinase negative L cells transformed by a cloned rabbit chromosomal β globin gene linked to the cloned gene of herpes simplex virus type 1. This cell line cannot, however, be used to test for tumorigenic properties for the cell line is transformed.

Wigler et al, *Cell*, Vol. 16, 777–785 (1979) discusses cotransfection for introduction of any defined gene into cultured cells.

Hampar et al, *Cancer Research*, 40:2213–2222 (1980) utilizes ultraviolet light irradiated herpes simplex virus in studying phenotypic properties of transformed cells.

Not prior art but pertinent to the invention: p Hampar et al, *Proc. Natl. Acad. Sci.*, 78:2616–2619 (April 1981) discusses producing clonal subline B2.

ABBREVIATIONS

HSV, herpes simplex virus; TK, thymidine kinase; tk, TK gene; HAT, TK-selective medium containing hypoxanthine, aminopterin, and thymidine; BrdUrd, 5-bromodeoxyuridine; IdUrd, 5-iodo-2'-deoxyuridine; UV-HSV, UV-irradiated HSV; PAA, phosphonoacetic acid.

STATEMENT OF DEPOSIT

A sample of the cell line, Cl.B2-1, derived from mutated 10E2 cells has been deposited with the American Type Culture Collection and has received number CRL 8085.

BACKGROUND OF THE INVENTION

Herpes Simplex Virus (HSV) is used to introduce genes into cells to assess their biological properties.

Screening or location of the gene of interest is based on the HSV-1 tk (thymidine kinase) gene.

The enzyme thymidine kinase (TK) catalyzes the initial step in a nonessential "salvage pathway" which allows mammalian cells to utilize extracellular thymidine (or its analogs) for incorporation into cellular DNA. In the absence of this "salvage" pathway, the cells have adequate machinery for synthesizing thymidine.

Cellular TK synthesis can be shut off by mutagenesis with an analog of thymidine such as 5-bromodeoxyuridine (BrdUrd) or 5-iodo-2-deoxyuridine (IdUrd). The resultant TK-negative cells can still survive and proliferate in normal growth medium but not in a selective medium containing hypoxanthine-aminopterin-thymidine (HAT), which prevents the endogenous synthesis of thymidine. In contrast, nonmutagenized cells which synthesize TK (TK-positive) can survive and proliferate in HAT medium by utilizing the extracellular thymidine, despite their inability to synthesize endogenous thymidine due to the inhibitory effects of HAT.

The herpes simplex virus (HSV) genome contains coding sequences for a viral TK whose biophysical and biochemical properties differ from those of the cellular TK. When one infects TK-negative cells with partially inactivated HSV and places the cells in selective HAT medium, TK-positive cells can be isolated which express the viral TK. These "biochemically" transformed cells by expressing the viral TK can survive in HAT medium. Biochemical transformation with HSV TK can also be effected by transfecting TK-negative cells with purified viral DNA or with the viral tk gene cloned in an appropriate vector.

The introduction and expression of the HSV tk gene into TK-negative cells facilitates detailed molecular studies on transcriptional and translational control mechanisms. This system also facilitates detailed studies of the biological function of non-tk genes introduced into TK-negative cells by co-transfection with the HSV tk gene. The co-transfected cells can be selected in HAT medium for TK activity and the presence of the non-tk gene ascertained by blot hybridization or assaying for translational products. Thus, the HSV tk gene can be used as a suitable vehicle for introducing non-TK genes into cells to assess their biological properties.

One of the uses of TK-negative cells and the HSV tk gene as a vehicle for co-transfection is to assess the tumorigenic potential of non-tk genes. To accomplish this requires the availability of a non-transformed TK-negative cell and evidence that the HSV tk gene itself does not have tumorigenic potential. Several TK-negative cells have been described, with the Ltk-mouse cell being used most frequently for "biochemical" transformation. All of these TK-negative cells have in common the property of being morphologically transformed and tumorigenic when inoculated into an appropriate host, thus precluding their use for assessing the tumorigenic potential of non-tk genes. In order to overcome this deficiency, a non-transformed TK-negative mouse cell is necessary. No non-transformed TK negative cell line had been developed prior to this invention.

SUMMARY OF THE INVENTION

A unique non-transformed thymidine kinaseless cell line which retains phenotypically normal properties with continuous subculture has been produced. BALB/c derived 10E2 cells were mutated by BrdUrd and maintained by IdUrd and cloned. One clonal subline (B2) was recloned and this clonal (Cl B2-1) has been subcultured over 65 times. No evidence of tumorigenic transformation can be found and the cell line based on Cl B2-1 cells is non-transformed.

The cell line was biochemically transformed using either UV-irradiated HSV-1(strain 14012) or the tk-containing BamHI fragment of HSV-1 DNA cloned in the plasmid pBr 322 to determine if the HSV tk gene is tumorigenic. The result is negative.

It was also determined that morphological and biochemical transformations by HSV are independent events. These results establish that the HSV-1 tk gene is a suitable vehicle for introducing non-tk genes into cells for assessing their tumorigenic potential. Studies with sarcoma gene as a gene of interest in this regard confirms this process. Non-tk genes for investigation as to their tumorigenic potential may be ligated or co-transfected with HSV tk gene into the unique B2-1 cell line and conventional testing reveals whether transformation occurs, thus determining tumorigenicity.

The usefulness of this procedure is clearly evident when one considers that many genes have no readily discernable marker and are "lost" in the cellular environment. But, with this invention, the gene of interest is always marked; and, of course, the important question of tumorigenicity of the gene of interest can be readily established.

DETAILS OF THE INVENTION

Materials and Methods. BALB/c-derived 10E2 cells were treated over a 12-month period with increasing concentrations of BrdUrd (0.5–100 μg ml$^{-1}$) using Eagle's minimal essential medium plus 10% heat-inactivated fetal calf serum and antibiotics. The BrdUrd-resistant cells showed a survival frequency of 10$^{-4}$ in HAT medium, indicating that the cells still retained residual TK activity, albeit at low levels. The BrdUrd-resistant cells were then exposed to increasing concentrations of IdUrd (a more potent mutagen than BrdUrd) over a three-month period (1–100 μg ml$^{-1}$) and were subsequently maintained on IdUrd at a concentration of 100 μg ml$^{-1}$. The IdUrd-resistant 10E2 cells were cloned by isolating well-dispersed colonies growing on plastic in the presence of IdUrd, and one clone (cl. B2) was selected for further study. The cl. B2 cells were subsequently recloned and cl. B2-1 cells were isolated.

The cl. B2-1 cells are subcultured at an 8:1 split ratio at weekly intervals. The cells show a TK-positive reversion frequency of $<0.3 \times 10^{-6}$ when tested in HAT medium after growth for one week in the absence of IdUrd. and a reversion frequency of $0.5 \times 10^{-5}$ when maintained for a period of 15 weeks in the absence of IdUrd. We can conclude that mutagenesis of cl. B2-1 cells to a TK-negative state did not result from deletion of the cellular tk gene.

The cl. B2-1 cells have now been subcultured over 65 times (approximately 200 cell doublings) and have retained a "normal" flat epithelioid appearance. The cells have been tested 15 times between subcultures 2 to 60 by inoculation of 10$^7$ cells subcutaneously into the anterolateral region of the dorsum of BALB/c nu/nu mice and have shown no evidence of tumorigenic transformation. Based on their morphology and lack of tumorigenicity, it is concluded tht cl. B2-1 cells are non-transformed.

Determination that HSV-tk gene is Non-tumorigenic—Transformation with UV-Irradiated HSV. B2 cells maintained for 1 week in the absence of IdUrd were seeded in replicate at $5 \times 10^5$ cells per 75-cm$^2$ flask. After 2–3 days, the cells were infected at an appropriate multiplicity of infection with HSV-1 (strain 14012) that had been UV-irradiated for various times at 63 ergs/mm$^2$ per sec (UV-HSV-1). The multiplicity of infection was determined prior to irradiation by titration in Vero cells. The cells were incubated for 2 hr, washed, and dispersed with trypsin. Cells were seeded in triplicate at $0.5$–$1.0 \times 10^5$ per 75-cm$^2$ flask for morphological transformation and at $1.0$–$5.0 \times 10^5$ for biochemical transformation. Phosphonoacetic acid (PAA) (20 μg/ml) (Richmond Drug, Richmond, VA) was added and was removed by refeeding on day 7. HAT was added to cultures used for biochemical transformation on days 3–4. All cultures were refed weekly. Biochemically transformed colonies were isolated after 4–6 weeks, and the cells were propagated in HAT. Morphologically transformed colonies of spindle-shaped cells were isolated after 8–12 weeks and one subculture.

Transformation with Viral DNA. B2 cells were transfected with HSV-1 tk cloned in plasmid pBR322 by using a modification of reported procedures [Wigler et al, *Proc. Natl. Acad. Sci. USA*, 76:1373–1376 (1979) and Parris et al, *Virology*, 100:275–287 (1980)]. Prior to transfection, the plasmid DNA was digested with either HindIII or BamHI and DNA solutions were prepared in 1 mM Tris/0.1 mM EDTA diluted in an equal volume of 0.5M CaCl$_2$. The DNA/Ca solution was added dropwise with bubbling to an equal volume of Hepes-buffered saline and was left at room temperature for 45 min. to allow precipitate formation. B2 cells ($2 \times 10^6$) placed in separate tubes were pelleted at $200 \times g$, and the supernatant fluids were aspirated, leaving behind a drop of fluid. The cell pellets were disaggregated in the remaining fluid by vigorous agitation using a vortex mixer. A 0.5-ml suspension containing 1–2 μg of digested DNA was added to each tube and the tubes were placed on a slowly rotating roller apparatus for 45 min. at 37° C. Growth medium (10 ml) was added to each tube and the cells were dispensed into four T-25 flasks containing additional growth medium. The cells were incubated at 37° C. and were refed with growth medium after 12–14 hr. After an additional 48 hr, the cells were refed with HAT. Surviving colonies were isolated after 4–6 weeks and were maintained with HAT.

Identification of Viral TK. Cells ($5 \times 10^4$) were seeded 2 days before testing in 16-mm cluster wells. Uptake of [$^3$H]thymidine (2 μCi/ml; 1 Ci=$3.7 \times 10^{10}$ becquerels) was measured in the presence of tetrahydrouridine (20 μg/ml) with or without iododeoxycytidine (10 μg/ml). Cells were incubated for 3 hr and then lysed with 0.3M NaOH. The DNA was precipitated with 10% (wt/vol) trichloroacetic acid and collected on glass fiber filters.

Isoelectric focusing for differentiating viral and cellular TKs was performed on slab gels as described by Kit et al, *Int. J. Cancer*, 13:203–218 (1974). Enzyme activity was determined by incubation on DE-81 paper followed by autoradiography as described by Maitland and McDougall, *Cell*, 11:233–241 (1977).

Infection of B2 cells by UV-HSV was carried out in the presence of PAA to reduce the breakout of infectious virus. The PAA was removed by refeeding after 7 days. Morphologically transformed foci containing spindle-shaped cells were evident after one subculture of cells infected with UV-HSV (6-min irradiation) and seeded at a cell density of 10$^5$. The appearance of the transformed B2 cells was similar to that of spontaneous and UV-HSV-transformed 10E2 cells. Comparable foci containing spindle-shaped cells were not seen in control, uninfected B2 cultures. The 15 morphologically transformed foci isolated from UV-HSV-infected B2 cultures were tumorigenic in nu/nu mice (fibrosarcomas), but 10 areas of nontransformed cells isolated at random from control uninfected cultures were non-tumorigenic (Table 1). When inoculated (10$^7$ cells) into nu/nu mice, the control uninfected cell population also proved to be nontumorigenic. The cells in all morphologically transformed foci isolated from UV-HSV-infected B2 cultures were unable to incorporate [$^3$H]thymidine into cell DNA (determined autoradiographically), did not survive (10$^6$ cells) in HAT and were resistant (100 cells) to the toxic effects of IdUrd (100 μg/ml). Based on these criteria, it was concluded that the morphologically transformed cells were TK negative.

TABLE 1

Tumor Induction by UV-HSV Morphologically and Biochemically Transformed B2 Cells

| Infected by subculture | Virus MOI* | No. active foci/no. tested** Morphological | No. active foci/no. tested** Biochemical |
|---|---|---|---|
| 7 | 5 | — | 0/14 |
| 12 | 0 | 0/5*** | — |
|  | 3 | 7/7 | — |
| 19 | 3 | — | 0/21 |
| 24 | 0 | 0/5*** | — |
|  | 2 | 8/8 | — |
| 29 | 3 | — | 0/12 |

*Multiplicity of infection determined by virus titration in Vero cells prior to UV irradiation.
**Tumorigenicity was tested in BALB/c nu/nu mice by inoculating $10^7$ cells subcutaneously in the anterolateral region of the dorsum. Five animals were used for each sample and they were observed for 10 weeks. All morphologically transformed cells were TK negative. All biochemically transformed cells expressed only the viral tk.
***Nontransformed cells were isolated at random from control cultures.

B2 cells were also biochemically transformed with the tk-containing BamHI fragment of HSV-1 DNA and the presence of the viral tk was confirmed (see above). The efficiency of transformation with B2 cells (1.6 colonies per $5 \times 10^5$ cells per 0.1 μg of DNA) was approximately 1/10th that observed with LTK$^-$ cells. The biochemically transformed B2 cells showed no evidence of morphological transformation, and the 15 cell lines tested showed no tumorigenic potential in nu/nu mice.

NEGATIVE CONTROL

The efficacy of B2-1 cells for determining the transforming potential of non-TK genes was assessed in two ways. First, B2-1 cells were biochemically transformed with uv-irradiated herpes simplex virus, and TK-converted cells were selected in HAT medium. Over 50 clones were isolated and shown to contain the HSV-TK gene. All of the clones were tested repeatedly in nu/nu mice and shown to be nontumorigenic. Several clones were then selected for testing by Southern blot hybridization to determine which fragments of the HSV genome were retained in the cells. One clone (2H-4) contains the HSV-TK gene and the adjacent R1(F) and R1(G) fragments. These fragments lie on either side of the TK gene. The results indicate that B2-1 cells can retain the F and G fragments of the HSV-1 genome without showing properties of tumorigenically transformed cells. This experiment serves as a negative control to show that one can introduce non-transforming gene sequences in B2-1 cells.

POSITIVE CONTROL

A second experiment involved introduction into the B2-1 cells of the HSV-TK gene in concert with a sarcoma gene from a murine sarcoma virus (MSV). The TK-converted cells were selected and shown to contain the viral TK gene and studies indicate that the cells show tumorigenic potential. It is thus a result that one can introduce a known transforming gene into B2-1 cells in concert with the herpes TK gene and the cells will express the transformed properties attributable to the non-TK gene.

STATEMENT OF UTILITY

The present invention shows a method for testing non-transforming genes such as are obtained by treating BALB/c derived 10E2 cells with 5-bromodeoxyuridine and 5-iodo-2'-deoxyuridine to produce thymidine kinaseless cells which, upon multiple cloning, show a flat epitheloid appearance indicative of their non-transforming potential. Where the cells are non-transformed, it is indicative of non-tumorigenic potential.

We claim:

1. A method for the determination of the tumorigenic or morphological transforming potential of a non-thymidine kinase (TK) gene comprising, introducing a non-TK gene and a TK gene into an animal cell line which lacks TK and is non-tumorigenic and not transformed morphologically by co-transformation or transformation of ligated genes, selecting for TK containing cells and, testing the resulting cells for tumorigenic potential in animals or phenotypic expression of morphological transformation in vitro.

2. A method according to claim 1 where the cell line lacking TK has all the identifying characteristics of ATCC CRL 8085.

3. A method according to claim 1 where the cell line lacking TK is produced by the process of exposing TK containing cells to at least one pyrimidine analogue capable of selecting for cells which lack TK activity, selecting and isolating a morpholigically non-transformed, non-tumorigenic animal cell line lacking TK and, cloning the resulting isolated cell line.

4. A method for preparing morphologically non-transformed, non-tumorigenic animal cells which lack thymidine kinase (TK) comprising, exposing TK containing cells to at least one pyrimidine analogue capable of selecting for cells which lack TK activity, selecting and isolating a morphologically non-transformed, non-tumorigenic animal cell line lacking TK and, cloning said isolated cell line.

5. A method according to claim 4 where the pyrimidine analogues are 5-bromodeoxyuridine and 5-iodo-2-deoxyuridine.

6. A method according to claim 5 where the cells are exposed to 5-bromodeoxyuridine before exposure to 5-iodo-2-deoxyuridine.

7. A method according to claim 4 where the concentration of pyrimidine analogue is gradually increased during exposure.

8. A cell line produced by the process of claim 4, 5, 6 or 7.

9. A non-transformed, non-tumorigenic thymidine kinase lacking cell line having all the identifying characteristics of ATCC CRL 8085.

* * * * *